US007727116B2

(12) United States Patent
Kaplan et al.

(10) Patent No.: US 7,727,116 B2
(45) Date of Patent: Jun. 1, 2010

(54) APPARATUS AND METHOD FOR THE TREATMENT OF COMPUTER VISION SYNDROME

(76) Inventors: George H. Kaplan, 2901 S. Skyline Dr., Inverness, FL (US) 34450; Timothy R. Nee, 8312 N. Elkcan Blvd., Citrus Springs, FL (US) 34433

(*) Notice: Subject to any disclaimer, the term of this patent is extended or adjusted under 35 U.S.C. 154(b) by 1164 days.

(21) Appl. No.: 11/316,767

(22) Filed: Dec. 23, 2005

(65) Prior Publication Data

US 2007/0037664 A1 Feb. 15, 2007

(51) Int. Cl.
*A61B 3/00* (2006.01)

(52) U.S. Cl. ............................ 482/1; 434/258; 351/203

(58) Field of Classification Search ................. 482/1–9, 482/900–902; 351/203, 223, 222; 434/258, 434/247, 271

See application file for complete search history.

(56) References Cited

U.S. PATENT DOCUMENTS

| | | | | |
|---|---|---|---|---|
| 4,534,557 | A | 8/1985 | Bigelow et al. | |
| 4,627,620 | A | 12/1986 | Yang | |
| 4,824,237 | A | 4/1989 | Ratner et al. | |
| 5,221,243 | A | 6/1993 | Walker | |
| 5,233,988 | A | 8/1993 | Raghuprasad | |
| 5,271,627 | A | 12/1993 | Russell et al. | |
| 5,803,745 | A | 9/1998 | Kozak et al. | |
| 5,812,239 | A | 9/1998 | Eger | |
| 6,364,485 | B1 * | 4/2002 | Fateh | 351/203 |
| 6,371,931 | B1 | 4/2002 | Guillen | |
| 6,533,417 | B1 * | 3/2003 | Sain | 351/203 |
| 7,347,694 | B2 * | 3/2008 | Berger et al. | 434/258 |
| 2001/0028437 | A1 * | 10/2001 | Beresford et al. | 351/203 |
| 2003/0081176 | A1 * | 5/2003 | Stewart | 351/223 |
| 2004/0049124 | A1 | 3/2004 | Kullok et al. | |

* cited by examiner

*Primary Examiner*—Glenn Richman
(74) *Attorney, Agent, or Firm*—Martin Fleit; Paul D. Bianco; Fleit Gibbons Gutman Bongini & Bianco PL

(57) ABSTRACT

Apparatus and method for the treatment of computer vision syndrome using a computer including a screen, a processor, memory and an I/O device. A set of instructions for the computer that includes programs for conducting hand-eye exercises in preselected sequences are loaded into the computer and run. Alternately, a pair of hand wands having a handle at one end and an LED light positioned on the other end are held by a user in front of the computer and a plurality of slap switches having means for detachably attaching the slap switches to a surface are positioned relative to the user and the computer. The user through the use of the slap switches and the hand wands carry out sequences of exercises that will rehabilitate the user regarding computer vision syndrome. The results of the exercises are communicated wirelessly from the hand wands and the slap switches to the computer.

14 Claims, 4 Drawing Sheets

APPARATUS AND METHOD FOR THE TREATMENT OF COMPUTER VISION SYNDROME

BACKGROUND OF THE INVENTION

1. Field of the Invention

The present invention relates to apparatus and method for the treatment of computer vision syndrome. More particularly, the invention relates to apparatus and method for the treatment and recovery of normal human performance lost due to trauma and/or injury, and post-traumatic injury and loss of normal performance of the human neuro-muscular, sensor-motor and psycho-physiological systems as a consequence of any physical and/or psycho-physiological "trauma/insult", but most particularly in regard to trauma or injury due to computer vision syndrome (CVS).

2. Prior Art

Many apparatuses and methods have been advanced for the treatment and recovery of normal human performance lost due to trauma and/or injury. These apparatuses and Methods seek to prevent, treat, protect, and reverse the discomfort and compromise imposed upon normal human functions (i.e., eye-hand coordination/reaction; eye movement; neuro-muscular tension; visual focusing; visual acuity; depth perception; peripheral vision; neuromuscular movement; vestibular function; equilibrium; perceptuo-motor function, visual/auditory spatia-orientation; and related psychological/emotional function) due to traumatic brain/neurological insult (including "Repetitive Stress Trauma") by means of a computer applied/assisted/presented/measured/analyzed regimen of programmed human "tasks and exercises" (i.e., Physical; Cognitive; Psychomotor; Kinesthetic; Proprioceptive, etc.) which are medically designed to rehabilitate, reestablish, reeducate, reinforce, and protect the Users normal range of comfortable, unrestricted function and performance in the User's surrounding real-world volume of three-dimensional unencumbered "free-space". Whereas the prior art apparatuses and methods deal with all general aspects of the problem, none offer a simple and effective apparatus and method for a computer user to deal with problems of CVS including computer tunneling vision.

SUMMARY OF THE INVENTION

It is the principal object of the present invention to provide a method and apparatus that can effectively treat and enhance recovery of normal human performance lost due to trauma and/or injury, particularly CVS, that performs in a simple and unobvious manner which is not apparent, obvious, or suggested, either directly or indirectly by any of the known prior art.

The foregoing is accomplished by the present invention through apparatus that comprises four essential subsystems, each separate, yet electronically and/or physically integrated and intercommunicating. Subsystem one comprises a standard desktop/portable personal computer (PC) with visual monitor, printer and standard I/O ports, including USB, Bluetooth, WiFi, IR, and any other available communicating software and hardware. Subsystem two comprises the software necessary for controlling and driving the PC and the other subsystems according to the User instructions for unique "exercises and tasks" (both graphically on-screen, off-screen and aurally via speakers and transducers) as will be described herein in detail; for graphically rendering User-performance data into storage or memory, and onto a visual monitor and/or printer; and, statistically analyzing and calculating and scoring User-performance instantaneously and over time, for the purpose of predicting treatment progress, so as to modify and customize further treatment for the User. Subsystem three is the actual electronic/physical human interface between User and the apparatus. Subsystem three generally consists of a plurality of small, ergonomically designed/shaped/sized devices that contain electronic circuitry and mechanical devices (lights, LEDs, switches, light-activated switches, sensors, detectors, transducers, gauges, sound transducers, USB cables, Bluetooth, WiFi, IR, etc.) that are free-standing, movable and lightweight for easy positioning. The manner of use will be described in detail in the following, and suffice it to say at this juncture that the User employs Subsystem three to interact with the PC according to the control of Subsystem two. Subsystem four is contained in subsystem three to effect the communication between subsystem three and the other subsystems and to control the operation of subsystem three.

The method of the present invention will become more apparent from the following detailed description of the invention.

Another object of the present invention is to provide an apparatus and method for the treatment and recovery of normal human performance lost due to trauma and/or injury that is easy to operate, and is computer driven and User-directed.

Another object of the present invention is to provide an apparatus and method for the treatment and recovery of normal human performance lost due to trauma and/or injury that is small, light-weight, easily transportable and easily adapted to any physical environment and location, i.e., at home, office medical-sports-rehabilitation facility and sports venue.

Another object of the present invention is to provide an apparatus and method for the treatment and recovery of normal human performance lost due to trauma and/or injury that is capable of "storing/graphing" current User performance results and outcomes for future reference; statistically analyzing performance and outcomes; and statistically predicting trends and future outcomes so as to accurately design, direct and customize future rehabilitation exercises to maximize benefits for each User.

Another object of the present invention is to provide an apparatus and method for the treatment and recovery of normal human performance lost due to trauma and/or injury that enables the User to maximize/accelerate/embed the "transfer" of the newly relearned skills into the User's unfettered, unencumbered "real world space" by utilizing exercises/tasks, techniques, elements that "extend" the User's "focus, attention, movement, activity" into the full dimensions of the User's Three-Dimensional (x, y and z axis) surrounding volume of "free-space", thereby removing the User's "Repetitive-Attention-Activity" off-and-away from the confining two-dimensional, fixed-distance, static, narrowed space of the "computer-monitor" environment.

Another object of the present invention is to provide an apparatus and method for the treatment and recovery of normal human performance lost due to trauma and/or injury that fully, directly and necessarily employs/trains the full array of the human sensory, psycho-physiological and neuro-muscular systems/modalities for the treatment of said symptoms and conditions. Specifically, these systems/modalities include those of: Tactile, Kinesthetic, Proprioceptive, Vestibular, Visua-visuo-motor, Auditory and Perceptuo-motor.

Another object of the present invention is to provide an apparatus and method for the treatment and recovery of normal human performance lost due to trauma and/or injury that enables the User to "self-direct", monitor and interpret his/her own treatment program by means of educational/instructional software "downloads" and interaction with a central processing internet website.

Another object of the present invention is to provide an apparatus and method for the treatment and recovery of normal human performance lost due to trauma and/or injury that enables the User's performance to be "remotely" directed/analyzed via internet/computer/LAN downloads/uploads to a central processing internet/LAN website/location.

Another object of the present invention is to provide an apparatus and method for the treatment and recovery of normal human performance lost due to trauma and/or injury that enables exercises/tasks to be carried into the User's surrounding volume of "free space" by employing unlimited combinations, complexities, mixes and blends of "on-screen" and "off-screen" activities, providing "single attention" tasks and "divided attention" tasks.

Another object of the present invention is to provide an apparatus and method for the treatment and recovery of normal human performance lost due to trauma and/or injury that enables the treatment of an unlimited number of "conditions" concurrently. For example, "exercises and tasks" that target Computer Vision Syndrome can be paired with "exercises and tasks" that target Carpel Tunnel Syndrome and Peripheral Vision, so that the exercises can be carried out simultaneously.

Another object of the present invention is to provide an apparatus and method for the treatment and recovery of normal human performance lost due to trauma and/or injury that enables continuous and unlimited modification and expansion capabilities of the "exercise and tasks" via inexpensive equipment upgrades, and software programming directed by the User, and by internet downloads.

Another object of the present invention is to provide an apparatus and method for the treatment and recovery of normal human performance lost due to trauma and/or injury that enables the greatest degree of "sensori-motor integration" via the unlimited ability to combine/mix/blend each specific "exercise and task" with any other specific "exercise and task(s)" so as to create "super/macro exercises and tasks" that train/reinforce several systems/modalities concurrently.

Another object of the present invention is to provide an apparatus and method for the treatment and recovery of normal human performance lost due to trauma and/or injury that enables the ability to train/reinforce all manners of oculomotor movement, including, but not limited to, smooth pursuits, saccades, convergence, depth perception, divergence, versions, rotations, focus by employing specific on-screen and off-screen "exercise and task(s)". Further, these "exercise and task(s)" can be carried out in all directions of gaze, with any head positions, and while the User is in any posture (standing, sitting, while moving, etc.).

Another object of the present invention is to provide an apparatus and method for the treatment and recovery of normal human performance lost due to trauma and/or injury that enables the direct training/reinforcement of the User's "usable/cognitive" peripheral vision and cognitive awareness of his/her surrounding volume of visual space.

Another object of the present invention is to provide an apparatus and method for the treatment and recovery of normal human performance lost due to trauma and/or that enables the direct training/reinforcement of the User's "usable/cognitive" peripheral vision and cognitive awareness of his/her surrounding volume of space for the purpose of: Increasing depth perception; increasing spatial localization; increasing visuo-vestibular function; increasing movement-detection; increasing eye-hand-auditory response/reaction; increasing the appreciation of "slow-motion" perception.

Another object of the present invention is to provide an apparatus and method for the treatment and recovery of normal human performance lost due to trauma and/or injury that enables the training/reinforcement of all manners of eye-hand coordination-reaction-speed-accuracy into all directions of visual gaze, and from all postures and positions that User may be in.

Another object of the present invention is to provide an apparatus and method for the treatment and recovery of normal human performance lost due to trauma and/or injury that enables the training/reinforcement of all manners of auditory-hand coordination-reaction-speed-accuracy into all directions of the Users surrounding space, and from all postures and positions that the User may be in.

Another object of the present invention is to provide an apparatus and method for the treatment and recovery of normal human performance lost due to trauma and/or injury that enables all manners of treatment/training of hand-wrist-arm-shoulder movement/articulation so as to prevent/rehabilitate repetitive use syndrome conditions.

Another object of the present invention is to provide an apparatus and method for the treatment and recovery of normal human performance lost due to trauma and/or injury that enables for the unlimited physical arrangement/configuration/setup of the training environment/station via the ability to freely move/rearrange/reattach the "wireless" elements of invention (Hand Wands, Slap Switches, etc.) into new and novel positions relative to the User, as determined by treatment demands and protocols.

Another object of the present invention is to provide an apparatus and method for the treatment and recovery of normal human performance lost due to trauma and/or injury that enables unlimited expansion/modification of all aspects of the apparatus by simple physical upgrades/expansion modules, and software upgrades via Internet.

Another object of the present invention is to provide an apparatus and method for the treatment and recovery of normal human performance lost due to trauma and/or injury that enables LAN-Based, User-to-User "interaction" so as to allow two or more Users to work simultaneously and in a teamwork manner.

Another object of the present invention is to provide an apparatus and method for the treatment and recovery of normal human performance lost due to trauma and/or injury that is more universally functional in today's market than the prior art devices.

It is intended that any other advantages and objects of the present invention that become apparent or obvious from the detailed description or illustrations contained herein are within the scope of the present invention.

The foregoing has described, in general, aspects of the invention and serves as an aid to better understanding the more complete detailed description which is to follow. The present invention is not limited to the exactly described method or exactly described detail of construction, fabrication, material, application, and any other variation of fabrication, use, or application as would be suggested or evident to a person of ordinary skill in the art from the teachings herein should be understood as an alternative embodiment of the present invention. Other and further advantages and objects of the invention will become more evident form the following detailed description of preferred embodiments of the invention when taken in conjunction with the appended drawings.

DETAILED DESCRIPTION OF PREFERRED EMBODIMENTS OF THE INVENTION

Figure 1:
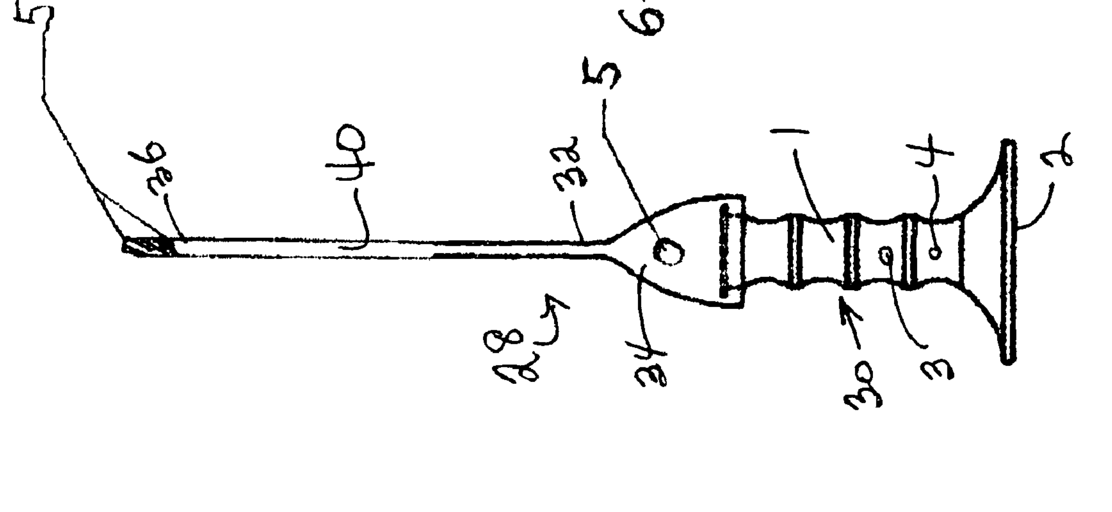
FIG. 1. is a front view of a hand wand according to the apparatus of the present invention for the treatment and recovery of normal human performance lost due to trauma and/or injury.

The purpose of the present invention is to provide a new apparatus and method for the treatment and recovery of normal human performance lost due to trauma and/or injury that has many novel features not offered by the prior art apparatus that result in a new apparatus and method for the treatment and recovery of normal human performance lost due to trauma and/or injury which is not apparent, obvious, or suggested, either directly or indirectly by any of the prior art apparatus.

As shown in the Figures and described hereinafter in detail, the invention provides an inexpensive and simple, free-standing, User-interactive apparatus and method for the treatment, management, relief and prevention of "Computer Vision Syndrome" and/or "Repetitive Use Syndrome", and can be used in combination with a treatment for "Carpal Tunnel Syndrome". Essentially, the invention corrects the manifold effects that traumatic brain injury and neurological insult have upon human performance and function as described elsewhere in this disclosure. The apparatus is designed to be used in conjunction with a common computer in the home or office workspace; and/or adapted, in a more complex manner, to be used in a medical/sports rehabilitation facility (physical/occupational/sports rehab centers). The apparatus is small, easily transportable and transferable between different computers. It is software-driven; User programmable (and programmable via Internet down-loads); and customizable to meet the specific requirements of each individual User's condition, symptoms, needs and current state of performance. Further, it is programmable to store and statistically analyze User performance data so as to determine current level of User performance; compute change/improvement-over-time"; as well as predict/direct future "outcomes". Generally, the apparatus consists of a computer (with monitor), appropriate software and several separate devices that are held by the User and are ergonomic, hand-holdable, actuatable, lightweight, and electrified or that are free-standing and positioned by the User. Each device houses a one or more lights (LEDs) and other signaling/sounding transducers that the User can see and/or hear, and communication circuitry, such as hardwired to the computer or interacting via wireless communication. Furthermore, each device houses one or more switches that the User can trip/trigger/activate. Furthermore, each device houses transducers/sensors that detect/measure any changes imposed upon its physicality, i.e., position, motion, acceleration and tilt. Furthermore, each device contains electronics that are programmed to send and receive impulses wirelessly or by hardwire to and from the computer, respectively, in a manner such that the computer activates LED(s) or other transducers (according to a computer program), and, subsequently, the User "responds" to the LED(s) or other transducers by "signaling back" to the computer via tripping/triggering/tilting/moving/rotating (or imposing other manipulation) upon the device. The computer is programmed to instruct, direct, motivate and elicit certain physical responses/exercises from the User. The type of physical responses/exercises directed by the computer program fall into the medical category of neuro-muscular; sensori-motor; kinesthetic; psycho-motor rehabilitation and relearning, which is currently the mainstay of occupational rehabilitation, physical rehabilitation and sports rehabilitation. In one specific example of the use of the invention, an embodiment of the method will treat Carpel Tunnel Syndrome. In this case the User will manually hold the wands (described above) in his/her hands. Then the computer will present written or animated instructions (via monitor) to the User as to what the starting position is, and in what manner the wands must be held. Then the computer will present progressive instructions to the User (via monitor) as to the medically designed hand/finger/wrist/arm exercises and motions necessary to treat/prevent Carpel Tunnel Syndrome.

In another example, an embodiment of the method will treat Computer Vision Syndrome. In this case the User will manually hold the wands in his/her hands. Then, the computer will present written or animated instructions to the User as to what the starting position is, and in what manner the wands must be held. Likewise, the computer will then instruct the User as to what manner he/she must fixate their visual gaze/attention/focus. Then, the computer will present progressive instructions (programmed steps) to the User as to proper wand movement so as to elicit the medically designed eye movement-tracking-focusing exercises and motions to treat Computer Vision Syndrome. Furthermore, the electronics on-board each wand allow the computer to monitor and grade the quality of the User's actualized eye responses to the computer instructions.

In yet another example, an embodiment of the apparatus will treat deficient/constricted hand-eye coordination and accuracy. In this case the User will employ one or more slap switches" (described above). The computer will present written or animated instructions to the User as to the proper physical placement/arrangement of the slap switches relative to the User in his/her work station. Then, the computer will present progressive instructions to the User as to what manner he/she must fixate their visual gaze/attention/focus. Then, the computer activates LED(s) in each of the slap switches, in a programmed manner, thereby presenting a medically designed sequence or pattern of visual stimuli to the User, who then attempts to extinguish the visual stimuli with a fast and accurate hand-eye" movement (slap) to the top of each slap switch which extinguishes the LED(s), thusly triggering the next stimuli sequence. Then, the computer registers/records the User's speed/accuracy of each hand-eye movement and scores the results and presents to the User a graphical display of his/her performance.

In yet another example, an embodiment of the method will treat the constricted visual fields (a condition brought about by "over focus" and "visual fatigue" at a computer screen). In this case the User will employ one or more slap switches. The computer will present written and/or animated instructions to the User as to the proper physical placement/arrangement of the slap switches about the Users physical periphery. Then, the computer will display certain visual stimuli/tasks on the monitor that are designed to capture the User's straight-ahead attention, and then, simultaneously, the computer will activate the peripherally located slap switches. The computer instructs the User to keep his/her visual awareness on the monitor and out to the periphery at all times, and to extinguish by slapping the appropriate slap switch stimuli with a fast, accurate, peripheral hand-eye coordinated movement (slap) to the top of the selected slap switch to extinguish the LED(s), thusly triggering the next stimuli sequence.

In these ways and with unlimited permutations of these ways, the User will be relieved of the harmful symptoms/injury/harm/constriction of normal human performance/function resulting from activities, occupations or events that cause Repetitive Use Syndrome, Computer Vision Syndrome, Carpel Tunnel Syndrome, or other deleterious conditions inflicted by other traumatic insult, i.e., stroke, brain trauma, psycho-motor trauma, and/or other neurological insult The present invention is generally comprised of four (4) subsystems. Each is separate, yet electronically and/or physically integrated and intercommunicating. Subsystem one is a standard desktop/portable personal computer (PC) with visual monitor, printer and standard I/O ports, including USB, Bluetooth, WiFi, IR, etc.

Subsystem two is software for driving the apparatus; presenting to the User step-by-step instructions for exercises and tasks (both graphically on-screen in written or animated form, or off-screen and aurally via speakers and transducers; recording performance in memory, scoring performance and graphically rendering User-performance data onto a visual monitor and/or printer; and, statistically analyzing User-performance data to track actual User-performance over time, for the purpose of predicting trends and outcomes so as to modify and customize further treatment for the User.

Subsystem three is the actual electronic/physical human interfaces or devices between User and the computer for two-way active intercommunication. They generally consists of a plurality of small, ergonomically designed/shaped/sized devices that contain one or more electronic signaling members or units, such as lights, LEDs, switches, light-activated switches, sensors, detectors, transducers, gauges, sound transducers, USB cables, Bluetooth, WiFi, IR, etc. The devices are free-standing, movable and lightweight so that the User may hold, wear, strap-on, adorn, attach, position, locate or otherwise externally support them. The User, pursuant to instructions provided by the program controlling the computer, and at appropriate times, positions the devices, and subsequently presses, strikes, bends, pushes or otherwise moves and manipulates the devices so the computer, via the intercommunication, is able to detect, register, measure, grade and time the User-actualized exercises and tasks that are presented to the User via the selected program for controlling the computer.

The elements of subsystem three serve two essential functions. The first function is to receive signals/impulses sent from the computer pursuant to the selected program and in response thereto, to condition the device to trigger, prompt, signal and motivate the User, visually or aurally, to respond with the required neuromuscular and sensori-motor movements/responses necessary for the treatment of the harm imposed upon the User as a result of trauma. The second function is, pursuant to action by the User and in response thereto, to transmit signals back to the computer, indicative of, the actualized neuro-muscular and sensor-motor motions/responses carried out by the User, which thereby allows the apparatus to detect, record in memory, compare, and register the actualized physical motions/responses of the User against the exercise and task instructions and demands issued to the User by the programmed instructions. As the human body and mind is supremely complex in shape, physicality and function, a complete description of all possible devices and elements, physical adaptations, shapes and embodiments is not possible. The current art does, though, describe many of these, and these are available for modification and adaptation for the unique purposes of the novel apparatus and method of the present invention.

However, this disclosure provides the physical descriptions of two specific preferred embodiments, identified as a hand wand, and a slap switch, and will be described in detail below.

Subsystem four is a small enclosure, of possibly "thumb-drive" dimensions, containing appropriate programmed electronics that electronically connects the devices with the computer, for example either hardwired to it or wirelessly by any known wireless communication system, such as, via standard input/output ports/cables, and/or wireless, USB, Bluetooth, IR, WiFi, etc. This thereby enables duplex transmission/reception of signals between the computer and the devices. Subsystem four can be incorporated directly into the devices.

A description of a preferred hand wand now follows. The hand wand is shaped roughly like a standard computer joy stick in that it is roughly cylindrical in shape, has a long, natural, comfortable, hand-contoured grip, has a built-in base for standing upright without external support, is lightweight, holdable and movable. Furthermore, each wand houses several electronic components (including built-in power source) that allow the cabled or wireless communication (via Bluetooth, WiFi, IR, etc.) to the computer. Additionally, housed inside each Wand are detectors, sensors, strain gauges, accelerometers, position detectors, transducers, tilt sensors, potentiometers, magnetic/electronic proximity sensors/switches, switches, light activated switches, and others detectors that measure all manners of changes imposed upon the position/physicality of the wand by the User. Additionally, each wand includes a built-in/molded-in elongated element, serving as the wand component, at the end of which are located one or several strategically placed lights/LEDs, situated in a manner that allows easy visibility to the User from all tilts and viewing angles within a forward facing hemisphere or 180 degree spherical forward arc. Additionally, mounted upon each wand are one or several electrical, mechanical, pressure, transductive, resistive-sensitive switches/activators that are strategically and ergonomically situated upon the wand that allows comfortable, natural, ergonomic actuation by the User by using any means.

A description of a preferred slap switch now follows. Each slap switch is shaped roughly similar to a disc approximating the size of a hockey puck. Each slap switch is roughly cylindrical in shape, is short in height relative to its overall diameter, has a natural, built-in base for standing upright without external support; is lightweight, holdable and movable. Furthermore, each slap switch houses several electronic components (including built-in power source) that enables cabled or wireless communication (via Bluetooth, WiFi, IR, etc.) to the computer. Additionally, housed inside each slap switch are detectors, sensors, strain gauges, accelerometers, position detectors, transducers, tilt sensors, potentiometers, magnetic/electronic proximity sensors/switches, switches, light-activated switches, and others that measure all manners of changes imposed upon the position/physicality of the slap switch by the User. Additionally, mounted onto each slap switch are attached/built-in/molded-in one or several strategically located lights/LEDs, situated in a manner that allows easy visibility to the User from all tilts and viewing angles. Additionally, upon each slap switch are one or several electrical, mechanical, pressure, transductive, proximity, resistive sensitive switches that are strategically and ergonomically situated upon the slap switch that allows comfortable, natural, ergonomic actuation by the User by using any one of the five fingers, as well as the palm of the hand, as well as, any other part of the human body, e.g. the foot, elbow and the like, as well as, by any other physical intermediary or means. Furthermore, for attaching the slap switches to various locations, positions and surfaces (relative to the User, i.e., horizontal/vertical and proximal/distal), one of the following, or a combination thereof is attached or fixed on the base or sides of each slap switch, a magnet, an adherent substance, a sticky tape, a hook system, a strap, a Velcro system, etc.

Referring now descriptively to the drawings, the attached figures illustrate the apparatus and method of the present invention for the treatment and management of injury and compromise imposed upon human functioning and performance.

FIGS. 1-8 illustrate specific preferred embodiments of the inventive apparatus and method for the treatment and management of the injury and compromise imposed upon human functioning and performance due to trauma. According to the present invention, the novel apparatus and method act to prevent, treat, protect, and reverse the discomfort and compromise imposed upon normal human functions (i.e., eye-hand coordination/reaction; eye movement; neuromuscular tension; visual focusing; visual acuity; depth perception; peripheral vision; neuromuscular movement; vestibular function; equilibrium; perceptuo-motor function, visual/auditory spatial-orientation; and related psychological/emotional function) due to traumatic brain/neurological insult (including "Repetitive Stress Trauma") by means of a computer—applied/assisted/presented/measured/analyzed regimen of programmed human tasks and exercises (i.e., Physical; Cognitive; Psychomotor; Kinesthetic; Proprioceptive, etc.) which are medically designed to rehabilitate, reestablish, re-educate, reinforce, and protect the User's normal range of comfortable, unrestricted function and performance in the User's surrounding real-world volume of three-dimensional unencumbered free-space.

Figure 2:
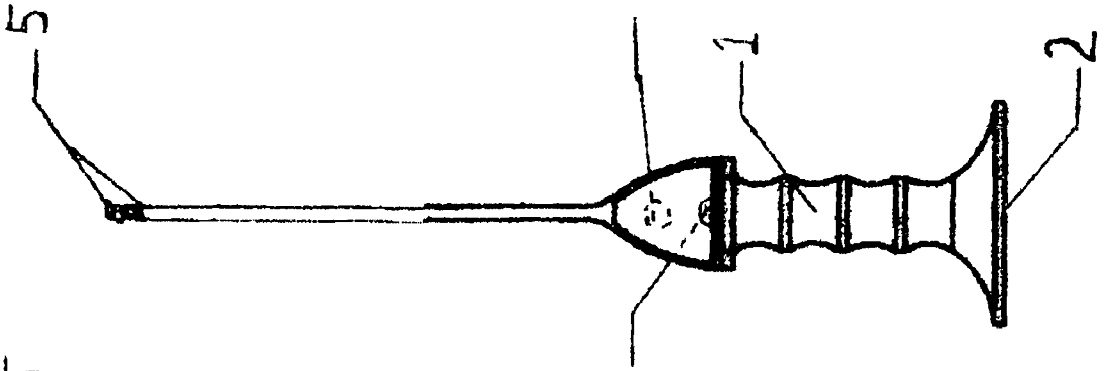
FIG. 2. is a rear view of the hand wand shown in FIG. 1.
Figure 3:
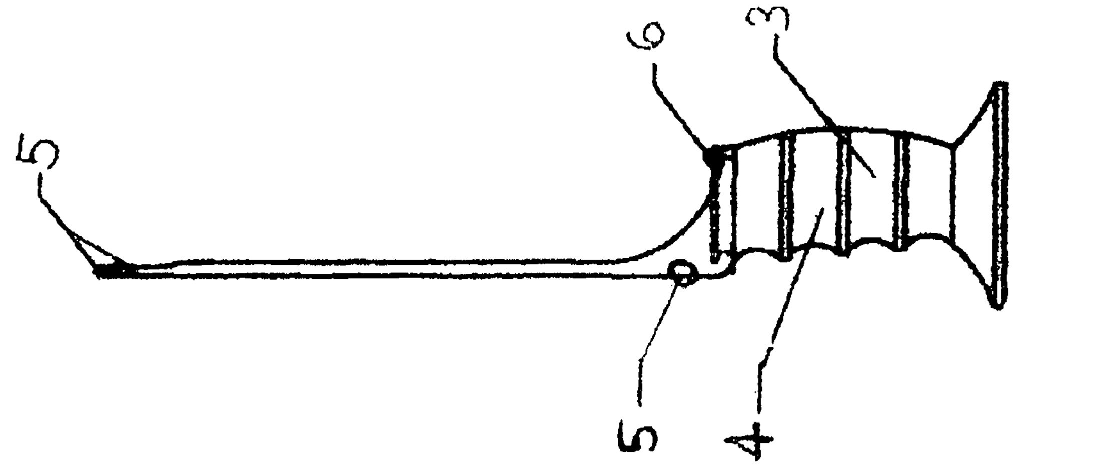
FIG. 3. is a side view of the hand wand shown in FIG. 1.

FIGS. 1 to 3 show three views of one specific preferred embodiment of a device referred to as a hand wand. The hand wand 28 shaped roughly like a standard joystick at a first end 30. The wand has an elongated, generally cylindrical shaped, naturally contoured, comfortable grip 1. Furthermore, the hand wand has a flat base 2 for standing upright without external support. Furthermore, housed inside each hand wand are the required known electronic components and built-in power supply 3 that enables a wireless two-way intercommunication with a computer. Additionally, housed inside each wand are known detectors, sensors, strain gauges, accelerometers, position detectors, transducers, tilt sensors, potentiometers, magnetic/electronic proximity sensors/switches, switches, light activated switches, and others, generally designated as 4, that measure all manners of changes imposed upon the position/physicality of the wand by the User. Additionally, each hand wand further comprises an elongated thin element 40 that is attached at one end 32 to the top 34 of the grip 1 and cantilever extends for a distance of about 1 to 3 feet. Mounted on the top 34 of grip 1 is at least one LED 5 that is electrically connected to the power source within the grip and to the two-way intercommunication with the computer, so that its activation can be controlled by the computer. There can be two or three LEDs of different color mounted to the end of the cantilevered thin element serving as the wand component. LED 5 at the free end 36 is electrically connected to the power source within the grip and to the two-way intercommunication with the computer, so that its activation can be controlled by the computer. The strategically located lights/LEDs 5, situated in a manner that enables easy visibility to the User from all tilts and viewing angles, are also controllable by a switch 6 in order to switch OFF, after having been switched ON by the computer. The switch 6 can be one of an electrical, mechanical, pressure, transductive, or resistive sensitive switch/activator that is strategically and ergonomically situated upon the wand that enables comfortable, natural, ergonomic actuation by the User by using any means. In this embodiment switch 6 is a spring loaded, depressible thumb switch.

Figure 5:
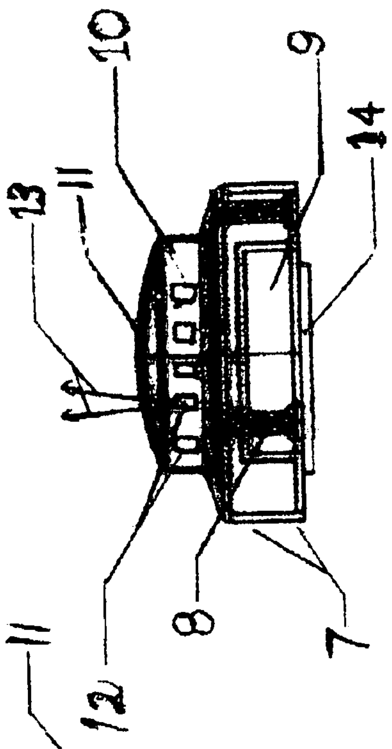
FIG. 5. is a side view of the slap switch shown in FIG. 4.
Figure 6:
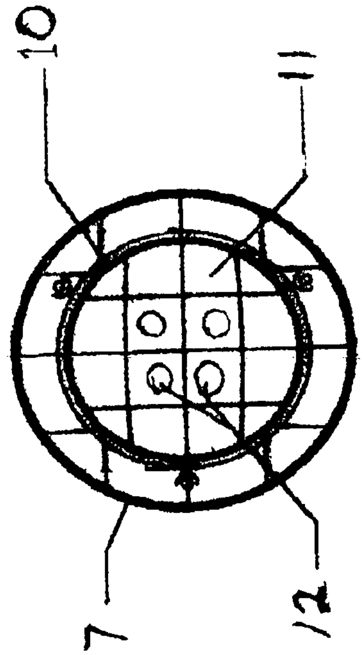
FIG. 6. is a top view of an alternative slap switch according to the apparatus of the present invention for the treatment and recovery of normal human performance lost due to trauma and/or injury.
Figure 4:
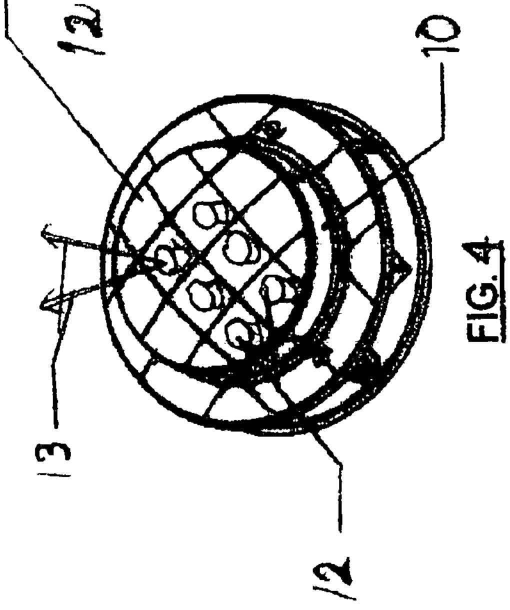
FIG. 4. is a perspective view of a slap switch according to the apparatus of the present invention for the treatment and recovery of normal human performance lost due to trauma and/or injury.

FIGS. 4 to 6, shows three views of another specific preferred embodiment of a device referred to as a slap switch. The slap switch is shaped roughly similar to a disc approximating the size of a hockey puck in that it is roughly cylindrical in shape, short in height relative to overall diameter, has a natural, built-in base 7 for standing upright without external support, is lightweight, holdable and movable. Furthermore, each slap switch houses several electronic components 8 (including built-in power source) that enables cabled or wireless two-way intercommunication (via Bluetooth, WiFi, IR, etc.) to the computer (see below). Additionally, housed inside each slap switch are several sensors 9 including detectors, sensors, strain gauges, accelerometers, position detectors, transducers, tilt sensors, potentiometers, magnetic/electronic proximity sensors/switches, switches, light-activated switches, etc. that measure all manners of changes imposed upon the position/physicality of the slap switch by the User. Furthermore, in this specific embodiment there is a large, depressible plunger switch 10 that is activated when the User pushes (slaps) down on it. Additionally, over the top of each plunger switch 10 is a plastic cap/cover 11 that is transparent/translucent to light. Furthermore, in this embodiment, there are several built-in/molded-in strategically located lights/LEDs 12 that are located within the body of the plunger switch 10, and that are aligned so that their light emissions 13 shine up and away from the body of the slap switch, and through the plastic cap/cover 11 of the plunger switch 10. Furthermore, upon the base of the slap switch is 14 a means of easy removable attaching of the slap switch to various locations, positions and surfaces (relative to the User, i.e., above, below, in front, peripherally, proximal, distal) comprised of any, or a combination of magnet, adherent substance/tape, hook system, strap, Velcro system, etc.

Figure 7:
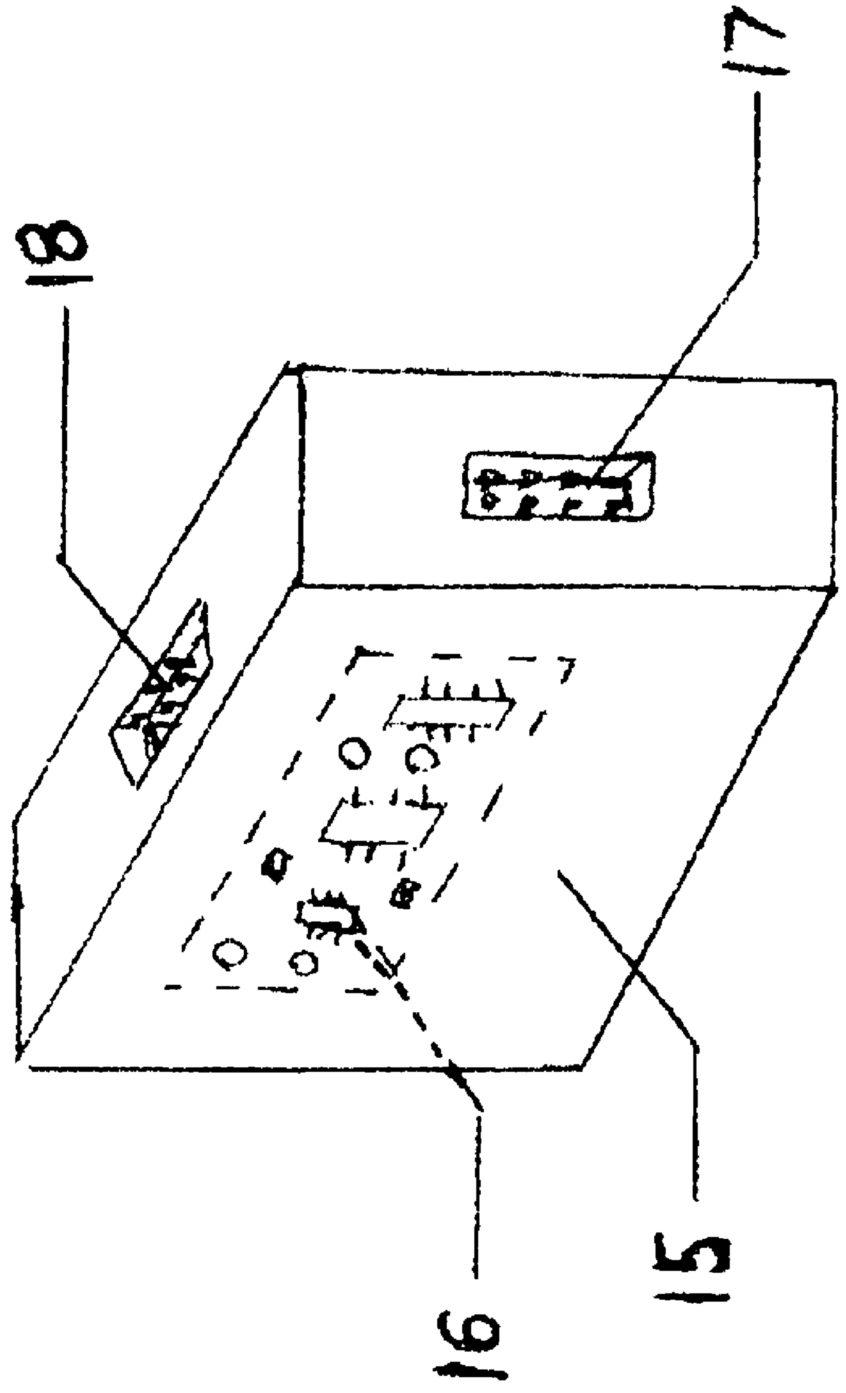
FIG. 7. is a perspective view of a control module according to the present invention.

FIG. 7 shows a perspective view of a small enclosure or box 15 (of possibly "thumb-drive" dimensions), which can be used as an alternative to incorporating the two-way intercommunication between the hand device, wand or slap switch, and the computer. Housed inside box 15 is the appropriate programmed electronic circuitry 16 that serves the purpose of electronically two-way interconnecting the hand held or activated devices and the computer via USB port 17 and cable/IR/Bluetooth port 18, respectively.

Figure 8:
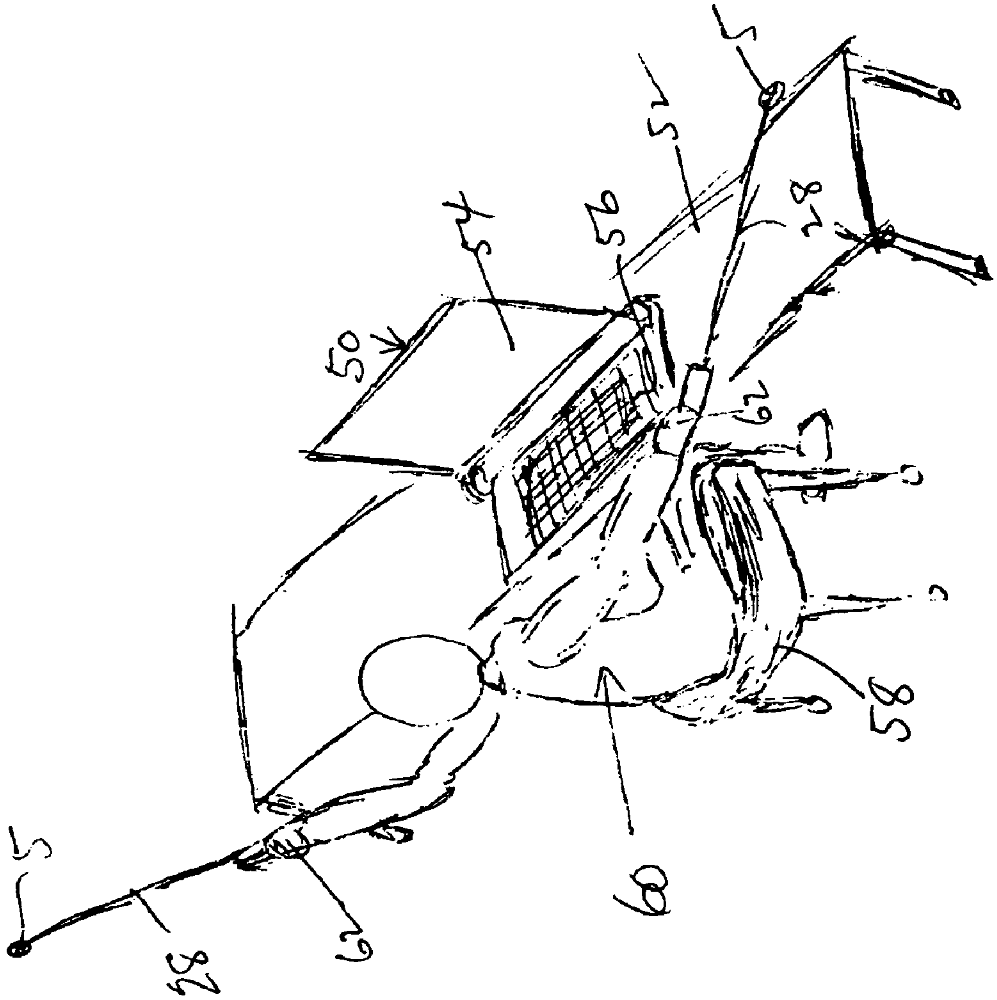
FIG. 8 is a schematic view showing the manner of use of the hand wand shown in FIGS. 1 to 3.

FIG. 8 shows a schematic view showing the manner of use of the hand wand shown in FIG. 1. As depicted, a computer 50, such as a laptop, is located on a table 52. The computer has a screen 54 and a keyboard 56 located on top of a case that contains the usual electronics. A User 60 sits on a chair or stool 58 in front of the computer and holds a wand 28 in each hand 62. Responsive to instructions graphically shown on the screen 54, either in as text or animatedly in graphic form, the User puts the wands 28 into defined or instructed positions whereupon the program lights up the LEDs 5, turns them ON, at the ends of the wands 28, either together or one at a time. The User, keeping his focus on a specific area of the screen as instructed, responds by peripherally detecting the turned ON lights, and then immediately by actuating the switch 6 on the wands 28 to extinguish or turn OFF the LED(s), whereupon a signal to that effect is communicated to the computer, stored in memory with data relevant thereto and the program steps to the next step. The steps of the program are controlled or selected according to the exercise to be performed.

To give effect to the present invention any general purpose computer or computer system including a set of Computer Nodes and/or Group Members can be employed. A typical group member can be a conventional desktop computer system, a conventional laptop computer system, a conventional workstation, or an IBM eServer iSeries server system. Any suitably configured processing system is similarly able to be used by embodiments of the present invention. The computer system has a processor that is connected to a main memory, mass storage interface, terminal interface and network interface. These system components are interconnected by a system bus. Mass storage interface is used to connect mass storage devices, such as a DASD device, to the computer system. One specific type of DASD device is a floppy disk drive, which may be used to store data to and read data from a floppy diskette.

The Main Memory contains application programs, objects, data and an operating system image. The applications programs, objects, data and operating system are not required to be completely resident in the main memory at all times or even at the same time. The computer system can utilize conventional virtual addressing mechanisms to allow programs to behave as if they have access to a large, single storage entity, referred to herein as a computer system memory, instead of access to multiple, smaller storage entities such as main memory and DASD device. Note that the term "computer system memory" is used herein to generically refer to the entire virtual memory of computer system.

The operating system is a suitable multitasking operating system such as the IBM OS/400 operating system. Embodiments of the present invention are able to use any other suitable operating system. Operating system includes a DASD management user interface program, a DASD storage management program and a group user interface program. Embodiments of the present invention can utilize architectures, such as an object oriented framework mechanism, that allows instructions of the components of operating system to be executed on any processor within the computer.

Computer systems with single or multiple CPUs can be used equally effectively. Embodiments of the present invention incorporate interfaces that include separate, fully programmed microprocessors that are used to off-load processing from the CPU. Terminal interface is used to directly connect one or more terminals to the computer system. These terminals, which are able to be non-intelligent or fully programmable workstations, are used to allow system administrators and users to communicate with the computer system.

A network interface can be used to connect other computer systems or group members, to the computer system. The present invention works with any data communications connections including present day analog and/or digital techniques or via a future networking mechanism.

Although the exemplary embodiments of the present invention are described in the context of a fully functional computer system, those skilled in the art will appreciate that embodiments are capable of being distributed as a program product via floppy disk, e.g. floppy disk, CD ROM, or other form of recordable media, or via any type of electronic transmission mechanism.

Embodiments of the present invention include an operating system that includes a DASD management user interface program that performs functions related to configuration, operation and other management functions, including functions for selecting one or more DASDs for an auxiliary storage pool (ASP). An ASP is defined as a set of disk units, and an independent auxiliary storage pool (IASP) is a set of disk units independent of a system. An IASP can be switched between systems, if its disk units are switchable and follow configuration and placement rules. The DASD management user interface program is able to communicate with DASD storage management (DSM) program, which is a component of operating system that provides internal support for managing disk units.

Non-limiting Software and Hardware Examples: Embodiments of the invention can be implemented as a program product for use with a computer system such as, for example, the cluster computing environment described herein. The program(s) of the program product defines functions of the embodiments (including the methods described herein) and can be contained on a variety of signal-bearing medium. Illustrative signal-bearing medium include, but are not limited to: (i) information permanently stored on non-writable storage medium (e.g., read-only memory devices within a computer such as CD-ROM disk readable by a CD-ROM drive); (ii) alterable information stored on writable storage medium (e.g., floppy disks within a diskette drive or hard-disk drive); or (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the present invention, whether implemented as part of an operating system or a specific application, component, program, module, object or sequence of instructions may be referred to herein as a "program." The computer program typically is comprised of a multitude of instructions that will be translated by the native computer into a machine-readable format and hence executable instructions. Also, programs are comprised of variables and data structures that either reside locally to the program or are found in memory or on storage devices. In addition, various programs described herein may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

It is also clear that given the typically endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.) It should be appreciated that the invention is not limited to the specific organization and allocation or program functionality described herein. The present invention can be realized in hardware, software, or a combination of hardware and software. A system according to a preferred embodiment of the present invention can be realized in a centralized fashion in one computer system, or in a distributed fashion where different elements are spread across several interconnected computer systems. Any kind of computer system—or other apparatus adapted for carrying out the methods described herein—is suited. A typical combination of hardware and software could be a general purpose computer system with a computer program that, when being loaded and executed, controls the computer system such that it carries out the methods described herein.

Each computer system may include, inter alia, one or more computers and at least a signal bearing medium allowing a computer to read data, instructions, messages or message packets, and other signal bearing information from the signal bearing medium. The signal bearing medium may include non-volatile memory, such as ROM, Flash memory, Disk drive memory, CD-ROM, and other permanent storage. Additionally, a computer medium may include, for example, volatile storage such as RAM, buffers, cache memory, and network circuits. Furthermore, the signal bearing medium may comprise signal bearing information in a transitory state medium such as a network link and/or a network interface, including a wired network or a wireless network, that allow a computer to read such signal bearing information.

It will also be understood that, in addition to the use of the invention for the treatment and recovery of normal human performance lost due to trauma and/or injury, the invention can be used to improve and enhance normal human function to higher levels of performance for other desirable purposes, such as sports performance enhancement and other human endeavors that require peak human performance.

The use of the invention and the method will now be described in more detail with reference to specific examples. Slap switches are hockey-puck sized enclosures. Several are wirelessly connected to the computer. One can place or attach them anywhere within arms reach via Velcro straps or magnets. The computer lights them up one at a time (via LEDs 5), the user then slaps them with the palm of his hand, which (1) extinguishes the light, and (2) simultaneously triggers the computer to illuminate the slap switches in a preselected, preprogrammed sequence. And, so on.

This method of operation directs and triggers eye-hand coordination, reaction time, reaching accuracy, and peripheral vision, all of which a static computer environment suppresses.

Imagine, on your desk, you have placed four slap switches; one to your far right, another to your far left, one directly in front of the computer monitor, one attached to the top of the computer monitor. You are instructed to keep your visual gaze at a pixilated point on your computer monitor, AND simultaneously widen your peripheral awareness so that you can sense the position of each of the slap switches with your side vision. Now, the next step of the program causes the slap switch to your right to light up. You KEEP your gaze straight ahead on the computer monitor AND quickly and accurately move your arm to the peripherally located switch, and slap it down. This trips the program to cause the left slap switch to light up. You repeat the above with your left hand. This causes the program then to trip the slap switch on top of the monitor to light. You KEEP your gaze straight ahead on the computer monitor AND quickly and accurately move your arm to the peripherally located switch, and slap it down. Then, the program steps to the next operation and causes the slap switch on the desk in front of monitor lights up, etc. In effect, the slap switches force you to keep your peripheral vision open, and forces you to keep your eye-hand circuits open, and forces your attentional mechanisms OFF of the computer screen, and into the surrounding volume of normal space.

The above scenario is very simple, but it illustrates the method and the use of the novel apparatus. We can increase the difficulty levels by adding slap switches, relocating their positions to stress the neuromuscular system, modifying the on-off speeds and duty cycles, flashing the lights in many complex orders, by flashing more than one switch at a time, and so forth, the variations are infinite. The wands on the other hand, force you to keep your eyes and hands yoked together in synchrony because you are holding them and moving them into different directions in space.

Together, the slap switches and wands, and the manner of use to carry out the method of the present invention, provide for a complete re-integration of normal visual motor function, to counter and oppose the effects of CVS.

Regarding the soft ware, as well as, what the machine does, the following needs to be taken into account. All of the exercises that are required for the rehabilitation fall into the category of eye-hand, eye-motor, visual attention exercises. These exercises in general are well known, and commonly employed in rehabilitation facilities that treat post trauma patients, e.g., strokes, developmental delays, TBI, etc. For example, eye tracking, large eye movements (saccades) and focusing exercises have been around for many years. There is already software known and available that teaches these exercises by either using a TV, Computer monitor, or various prior art equipment. However, the novel apparatus and method of the present invention and the use of the hand wands and the slap switches are what is unique in design and what has wide-spread applicability.

The following sets forth exercises for stimulating hand-eye coordination.

A. Exercise for stimulating Eye-Hand Coordination (Slap Switch)

Set Up:

1. User sits facing the computer screen at a distance of approx 3 feet.

2. User positions two Slap Switches on the counter top, one off to the left-one off to the right, separated by approximately 2 to 3 feet, and designated "Right" and "Left", respectively. On the computer screen, an animation appears that issues exercise instructions to the user.

3. Purpose of Exercise: Extended use of computers causes "over focus" or "over concentration" of the visual system into an area that just covers the computer screen, or to even smaller segments of the computer screen. This causes a tunneling of vision and perception. Repetition of this kind of visual activity causes a learning effect that locks the User into this tunnel vision mode, and makes it difficult to transition back into a more natural, flexible peripheral vision state. Also, over-use of a keyboard similarly causes a constriction in larger eye-hand movements by "locking" the eyes-hands into a constricted, small motor movements for typing The slap switch exercises break-down the constrictions of "over focus" so that the symptoms of CVS do not become embedded.

4. Exercise Sequences:

Sequence I:

a. User sits at computer station with both hands together in "palm down" starting position.

b. On cue from the computer, User presses either slap switch to start sequence, then returns hand to starting position.

c. User keeps visual gaze straight ahead on a computer icon.

d. The slap switches begin to blink in tandem, and the computer animation asks the User to determine if both slap switches are simultaneously visible off to the sides in User's peripheral vision. (If not, then User is instructed to move the slap switches slightly closer until they are both visible onto the sides without having to directly look at them).

Sequence 2:

a. User affixes his visual gaze at an inert animation on the computer screen.

b. After a short period, the slap switches begin to blink in random order.

c. The animation then instructs User to quickly and accurately "slap" each slap switch as soon as it lights up WHILE KEEPING visual gaze on the screen.

d. After each "slap" the User returns his hand to the palm down starting position, readied for the next slap switch stimuli.

e. User is prompted to maintain a "straight-ahead" visual gaze on the computer screen icon, while simultaneously expanding his peripheral visual awareness of the blinking slap switches so as to increase reaction times and eye-hand accuracy scores.

Sequence 3 Peripheral Eye-Hand Exercises with Cognitive Distractions a. User continues Sequence 2, above.

b. Animation presents "cognitive tasks" on the computer screen, ranging from simple to complex. For example, a simple single-digit addition problem is presented on the screen WHILE the User is continuing the slap switch exercises (above).

c. User "mentally" computes the answer and speaks the response into a voice-recognition microphone assembly, while continuing the eye-hand exercises.

d. The computer registers/scores the correct, or incorrect, response THEN continues with another "problem" presentation.

e. The computer may increase the complexity of the "problems", and may present the animation in the center of the screen, or in any other random location of the screen (thereby inducing a visual search complexity into the exercise routine, and the animation may ask the User to increase/decrease the slap switch separation, all the while the User is responding to the slap switch presentation.

Via the above sequences, the User is forced to maintain straight-ahead visual attention WHILE simultaneously and actively exercising peripheral vision-eye-hand awareness, thus the User will have less loss of peripheral awareness and decreased computer-induced "tunnel vision".

B. Exercise for Stimulating Peripheral Vision

Set Up:

a. User sits facing the computer at a distance of approx 3 feet.

b. User holds one hand wand in each hand.

c. On the computer screen, an animation appears that issues eye-exercise instructions to the user.

Exercise Sequences:

Sequence 1:

a. User extends wands towards the startup icon in the middle of the screen.

b. User starts exercise routine by pressing the switch on each wand. Each wand will then flash in random order.

c. User is instructed to press the switch on the wand that is lighting up in order to either acknowledge the lighting or to extinguish the light.

Sequence 2 Determining Maximum Range of Peripheral Vision a. After a short period, each wand begins to blink simultaneously.

b. The animation then instructs User to slowly move both wands outwardly, towards his periphery.

c. User maintains a "straight-ahead" visual gaze on the computer screen icon, while simultaneously expanding his peripheral vision to maintain visual awareness of the blinking wand off to the sides.

d. This sequence is continued until the User has moved both blinking wands to the limits of his peripheral viewing ability, i.e., until they just disappear from view.

e. The User then brings the wands forward again, so they are just visible to the sides. This is called the "Maximum Peripheral Vision" (MPV).

f. User maintains the wands at the MPV, then, presses the switch on each wand, thereby signaling the computer to begin the next sequence.

Sequence 3 Exercising Peripheral Vision a. On the screen, the animation randomly points to either the right wand, or to the left wand, and simultaneously the LEDs also flash on-off in random.
b. User is to maintain visual gaze straight ahead on the computer screen, AND on the blinking LEDs located at the point of MPV.
c. The animation instructs the User as follows:
d. if the Animation points to a wand on which the LED is indeed lighted, the User is to press the Switch on the same wand.
e. if the animation 'points' to a wand on which the LED is NOT lighted, the User is to ignore the Animation and NOT press any switch.
f. The same Sequences are repeated for wands held in other positions (meridians), i.e., in the vertical meridians and diagonal meridians.

Via the above sequences, the User is forced to maintain straight-ahead visual attention WHILE simultaneously and actively exercising peripheral vision/awareness. Thus the User will have less loss of peripheral awareness and decrease computer-induced "tunnel vision".

It is further intended that any other embodiments of the present invention that result from any changes in application or method of use or operation, method of manufacture, shape, size, or material which are not specified within the detailed written description or illustrations contained herein yet are considered apparent or obvious to one skilled in the art are within the scope of the present invention.

What is claimed is:

1. Apparatus for the treatment of computer vision syndrome comprising:
a. a computer including a screen, a processor, memory and an I/O device;
b. a pair of hand wands having a handle at one end and an LED light positioned on the other end, each of said hand wands being operably associated with said computer;
c. a plurality of slap switches being connected to said computer and having means for detachably attaching the slap switches to a surface;
d. a set of instructions for the computer that includes programs for conducting hand-eye exercises in preselected sequences, the set of instructions loaded into the computer, e. wherein a user can be positioned before the computer and through the use of the slap switches and the hand wands carry out sequences of exercises that will rehabilitate the user regarding computer vision syndrome.

2. Apparatus according to claim 1 further including means for two-way communication between the computer and the hand wands and the slap switches.

3. Apparatus according to claim 2 wherein the hand wands and the slap switches include contact switches for initiating communication between the computer and the hand wands and the slap switches.

4. Apparatus according to claim 2 wherein the hand wands and the slap switches include detectors that detect preselected conditions for communication to the computer when communication is activated.

5. Apparatus according to claim 2 wherein the means for two-way communication is conducted wirelessly.

6. Apparatus according to claim 1 wherein the computer includes means for connection to the Internet for downloading program instructions relating to hand-eye exercises.

7. The apparatus according to claim 1, further comprising:

means for wireless two-way communication between said computer, said hand wands, and said slap switches;

said hand wands including contact switches for initiating communication between said computer sand said hand wands and further including detectors for detecting preselected conditions for communication to said computer when communication between said hand wands and said computer is active; and said slap switches including contact switches for initiating communication between said computer and slap switches and further including detectors for detecting preselected conditions for communication to said computer when communication between said slap switches and said computer is active.

8. Method for the treatment of computer vision syndrome comprising the steps of:

establishing a device according to claim 7;

loading the programs into the computer for conducting hand-eye exercises in preselected sequences;

positioning a user before the computer with one of said pair of hand wands in each hand;

carrying out a first series of exercises with the user manipulating the hand wands according to instructions issued by the computer, removing the hand wands from the user;

positioning the slap switches relative to the user in relation to the computer; and carrying out a second series of exercises with the user interacting with the slap switches according to instructions issued by the computer.

9. Method according to claim 8 including the further steps of interactively communicating between the computer and the hand wands and the slap switches.

10. Method according to claim 9 wherein the interactive communication is carried out wirelessly.

11. Method according to claim 8 including the further steps of detecting conditions of the hand wands and the slap switches and communicating the detected conditions with actuation of the actuating switches.

12. Method according to claim 8 including the further step of downloading into the computer exercise programs relating to hand-eye exercises from the Internet.

13. An apparatus for treating computer vision syndrome, comprising:

a computer including a screen, a processor, memory, and an I/O device;

a hand wand having a handle at a first end and an LED light positioned on a second end, said hand wand being connected to said computer;

a slap switch being connected to said computer and having a means for detachably attaching said slap switch to a surface; and a set of instructions to be run on said computer, said instructions including a program for conducting hand-eye exercises in a preselected sequence to rehabilitate computer vision syndrome, said hand-eye exercises utilizing said slap switch and said hand wand.

14. An apparatus for treating computer vision syndrome, comprising:

a hand wand having a handle at a first end and an LED light positioned on a second end, said hand wand being connectable to a computer;

a slap switch being connectable to the computer and having a means for detachably attaching said slap switch to a surface; and a set of instructions to be run on the computer, said instructions including a program for conducting hand-eye exercises in a preselected sequence to rehabilitate computer vision syndrome, said hand-eye exercises utilizing said slap switch and said hand wand.

* * * * *